(12) United States Patent
Bleyer et al.

(10) Patent No.: US 8,049,059 B2
(45) Date of Patent: Nov. 1, 2011

(54) MEDICAL GRAFT DEVICE WITH MESHED STRUCTURE

(75) Inventors: Mark W. Bleyer, West Lafayette, IN (US); Umesh H. Patel, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1271 days.

(21) Appl. No.: 10/493,458

(22) PCT Filed: Oct. 25, 2002

(86) PCT No.: PCT/US02/34337
§ 371 (c)(1),
(2), (4) Date: Sep. 24, 2004

(87) PCT Pub. No.: WO03/035125
PCT Pub. Date: May 1, 2003

(65) Prior Publication Data
US 2005/0021141 A1     Jan. 27, 2005

Related U.S. Application Data

(60) Provisional application No. 60/347,742, filed on Oct. 26, 2001.

(51) Int. Cl.
*A61F 13/00* (2006.01)
*A61F 2/10* (2006.01)
(52) U.S. Cl. ............... 602/47; 602/50; 623/15.12
(58) Field of Classification Search ............ 623/23.74, 623/15.12
See application file for complete search history.

(56) References Cited

U.S. PATENT DOCUMENTS

| | | | |
|---|---|---|---|
| 2,127,903 | A | 8/1938 | Bowen |
| 3,358,688 | A | 12/1967 | Tanner |
| 3,472,228 | A | 10/1969 | Tanner |
| 3,640,279 | A | 2/1972 | Brown et al. |
| 4,902,508 | A | 2/1990 | Badylak et al. |
| 4,956,178 | A | 9/1990 | Badylak et al. |
| 5,004,468 | A | 4/1991 | Atkinson |
| 5,275,826 | A | 1/1994 | Badylak et al. |
| 5,281,422 | A | 1/1994 | Badylak et al. |
| 5,352,463 | A | 10/1994 | Badylak et al. |
| 5,372,821 | A | 12/1994 | Badylak et al. |

(Continued)

FOREIGN PATENT DOCUMENTS

EP     0891165     4/2000

(Continued)

OTHER PUBLICATIONS

English translation of JP 9-047503 A.*

(Continued)

*Primary Examiner* — David H. Willse
(74) *Attorney, Agent, or Firm* — Woodard, Emhardt, Moriarty, McNett & Henry LLP

(57) ABSTRACT

A tissue graft product includes at least one collagen layer comprised of submucosa or renal capsule tissue having slits therein to provide a mesh pattern which in turn establishes a graft structure that is highly deformable. The slits and mesh pattern provide for improved characteristics when utilized as a tissue graft and in particular an external wound care. Preferred devices have multiple submucosa, renal capsule or other collagenous extracellular matrix layers, providing a substantial and lasting scaffold for tissue ingrowth during wound treatment.

35 Claims, 2 Drawing Sheets

U.S. PATENT DOCUMENTS

| | | | |
|---|---|---|---|
| 5,554,389 | A | 9/1996 | Badylak et al. |
| 5,641,518 | A | 6/1997 | Badylak et al. |
| 5,645,860 | A | 7/1997 | Knapp, Jr. et al. |
| 5,733,337 | A | 3/1998 | Carr et al. |
| 5,755,791 | A | 5/1998 | Whitson et al. |
| 5,955,110 | A | 9/1999 | Patel et al. |
| 5,968,096 | A | 10/1999 | Whitson et al. |
| 5,993,844 | A | 11/1999 | Abraham et al. |
| 5,997,575 | A | 12/1999 | Whitson et al. |
| 6,063,094 | A | 5/2000 | Rosenberg |
| 6,099,567 | A | 8/2000 | Badylak et al. |
| 6,171,344 | B1 * | 1/2001 | Atala .................. 623/23.64 |
| 6,206,931 | B1 | 3/2001 | Cook et al. |
| 6,475,232 | B1 | 11/2002 | Babbs et al. |
| 7,087,089 | B2 | 8/2006 | Patel et al. |

FOREIGN PATENT DOCUMENTS

| | | | |
|---|---|---|---|
| JP | 9-47503 A * | 2/1997 | |
| WO | WO 95/22611 | 8/1995 | |
| WO | WO 96/24661 | 8/1996 | |
| WO | WO 96/25179 | 8/1996 | |
| WO | WO 96/31226 | 10/1996 | |
| WO | WO 96/32146 | 10/1996 | |
| WO | WO 97/06837 A1 * | 2/1997 | |
| WO | WO 97/37614 | 10/1997 | |
| WO | WO 98/22158 | 5/1998 | |
| WO | WO 98/25544 A1 * | 6/1998 | |
| WO | WO 98/25636 | 6/1998 | |
| WO | WO 98/25637 | 6/1998 | |
| WO | WO 99/62431 | 12/1999 | |
| WO | WO 99/63051 | 12/1999 | |
| WO | WO 99/63051 A2 * | 12/1999 | |
| WO | WO 01/10355 | 2/2001 | |
| WO | WO 01/19285 | 3/2001 | |
| WO | WO 02/22184 | 3/2002 | |
| WO | WO 03/035125 | 5/2003 | |

OTHER PUBLICATIONS

English translation of JP9-47503 A (Kuroyanagi et al.).*
English translation of Kuroyanagi et al., JP 9-047503 A, published on Feb. 18, 1997 (duplicate listing for including publication date).*
American National Standard, ANSI/AAMI 10993-5:1993 "Biological Evaluation of Medical Devices, Part 5: Tests for Cytotoxity: in vitro Methods", Association for the Advancement of Medical Instrumentation. pp. 77-82, 10993-5:1993.
Clarke, K., et al. "Intestine Submucosa and Polypropylene Mesh for Abdominal Wall Repair in Dogs". *Journal of Surgical Research*, Jan. 1996; vol. 60, No. 1, pp. 107-114.
Gloeckner, D., et al. "Mechanical Evaluation and Design of a Multilayered Collagenous Repair Biomaterial", *Journal of Biomedical Materials Research*, Nov. 2000; vol. 52, No. 2. pp. 365-373. John Wiley & Sons, Inc. New York, NY, U.S.
Kropp, B.P., et al. "Experimental Assessment of Small Intestinal Submucosa as a Bladder Wall Substitute", *Urology*, Sep. 1995; vol. 46, Issue 3. pp. 396-400.
Lehtimaki, J., et al. "Neonatal Estrogenization of the Male Mouse Results in Urethral Dysfunction" *Journal of Urology*, Dec. 1996; vol. 156, No. 6. pp. 2098-2103.
Prevel, C.D., et al. "Small Intestinal Submucosa: Utilization for Repair of Rodent Abdominal Wall Defects". *Annals of Plastic Surgery*, Oct. 1995; vol. 35, No. 4. pp. 374-380. Little, Brown and Company.
Prevel, C.D., et al. "Small Intestinal Submucosa: Utilization as a Wound Dressing in Full-Thickness Rodent Wounds" *Annals of Plastic Surgery*, Oct. 1995; vol. 35, No. 4. pp. 381-388. Little, Brown and Company.
Whitson, B.A., et al. "Multilaminate Resorbable Biomedical Device Under Biaxial Loading". *Journal of Biomedical Materials Research*, Fall 1998; vol. 43, No. 3. pp. 277-281 John Wiley & Sons, Inc.
Xie, H., et al. "Use of Reconstructed Small Intestine Submucosa for Urinary Tract Replacement". *ASAIO Journal*, May-Jun. 2000; vol. 46, No. 3. pp. 268-272.
Notification of Transmittal of the International Search Report or the Declaration, PCT/US02/34337, Apr. 23, 2003.
PCT Written Opinion, PCT/US02/34337, Aug. 6, 2004.
Response to Written Opinion, PCT/US02/34337, Oct. 6, 2004.
Notification of Transmittal of International Preliminary Examination Report, PCT/US02/34337, Jan. 27, 2005.

* cited by examiner

MEDICAL GRAFT DEVICE WITH MESHED STRUCTURE

CROSS-REFERENCE TO RELATED APPLICATION

The present application claims the benefit of U.S. Provisional Application Ser. No. 60/347,742, filed Oct. 26, 2001 which is hereby incorporated by reference in its entirety.

BACKGROUND

The present invention relates generally to medical graft devices containing submucosa tissue. In particular, one embodiment of the present invention relates to a medical device comprising a collagen layer including submucosa, wherein the layer has a highly deformable, meshed structure.

As further background, certain extracellular matrix materials, including submucosa tissues, are known tissue graft materials. See, e.g., U.S. Pat. Nos. 4,902,508, 4,956,178, 5,281,422, 5,372,821, 5,554,389, 6,099,567, and 6,206,931. As taught in these patents, submucosa tissues from various biological structures such as small intestine, stomach, and the urinary bladder provide predominantly collagenous layers useful in a variety of surgical procedures where tissue support and/or ingrowth are desired. As one example, sheet-form submucosa tissue has been suggested and used as a wound dressing.

Modified tissue graft constructs, including certain perforated forms thereof, are also known. For example, U.S. Pat. Nos. 5,755,791 and 5,997,575 teach certain perforated submucosal tissue graft constructs. As taught in these patents, multilaminate submucosal tissue graft constructs may accumulate tissue fluid in cyst-like pockets between adjacent layers after implantation in soft tissue locations. To reduce the occurrence of such pockets, these patents teach that the multilayer submucosa graft constructs can be perforated.

Despite prior teaching of certain modified forms of submucosa grafts, needs remain for improved modified forms thereof, having particular utility for example in the treatment of open cutaneous wounds, including burns. The present invention is addressed to these needs.

SUMMARY OF THE INVENTION

In one preferred embodiment, the invention provides a tissue graft product comprised of a meshed layer of collagen including submucosa tissue or renal capsule tissue. Advantageous such products include at least one layer of submucosa having slits therein providing a mesh pattern, and wherein the mesh pattern provides to the submucosa or renal capsule layer an expansion ratio of at least about 1.2:1 when fully hydrated, preferably at least about 2:1. Desirably, the mesh pattern includes multiple generally parallel rows of slits, wherein the termini of the slits in adjacent rows are longitudinally offset from one another. Preferred mesh patterns will have the adjacent parallel rows of slits spaced from one another at a distance of about 1 mm to about 10 mm, more typically about 3 mm to about 7 mm. Individual slits within the mesh pattern can be of equal or differing lengths relative to other slits, and can have lengths of about 1 mm to about 20 mm, although other dimensions will also be useful and within the scope of the present invention. Most advantageous meshed products of the invention will have an overall collagen layer thickness of at least about 150 microns, usually within the range of about 150 microns to about 1000 microns, which can be provided for example by two or more layers of vertebrate submucosa tissue or renal capsule tissue bonded together to form a substantially unitary collagen layer. In other embodiments, the invention provides medical products that include such a meshed tissue graft product contained within sterile medical packaging.

Another preferred embodiment of the invention provides a method for grafting a patient, comprising grafting a patient with a tissue graft product as described above. A specific, particularly advantageous method involves the treatment of externally exposed wounds, such as burn wounds to the skin. Highly-exuding skin wounds, including burns and ulcers, can be treated particularly effectively with meshed submucosal or renal capsule products having an overall layer thickness of at least about 150 microns, in order to provide a lasting scaffold for wound coverage as well as tissue repair and/or ingrowth. Thus, such wounds are desirably treated with a meshed product having a collagen layer comprising at least two bonded submucosa and/or renal capsule layers in accordance with the invention. Preferred, meshed products of the invention will include a plurality of closely-spaced slits or holes sufficient in number and spacing to allow drainage of the exudate from burn, ulcer or other highly fluidized wounds and prevent the graft from being carried out of contact with the wounded tissue by such exudate.

Still another preferred embodiment of the invention provides a method of manufacturing a tissue graft product, comprising the steps of providing a collagen layer comprised of submucosa or renal capsule tissue, and producing in said layer a plurality of slits, said slits providing a mesh pattern as discussed hereinabove. The meshed product can then be sterilized and packaged to provide a medical product.

The present invention provides improvements in tissue grafts, medical products, and methods of their manufacture and use. Additional features and objects of the invention will be apparent from the descriptions herein.

DESCRIPTION OF THE PREFERRED EMBODIMENTS

Figure 1:
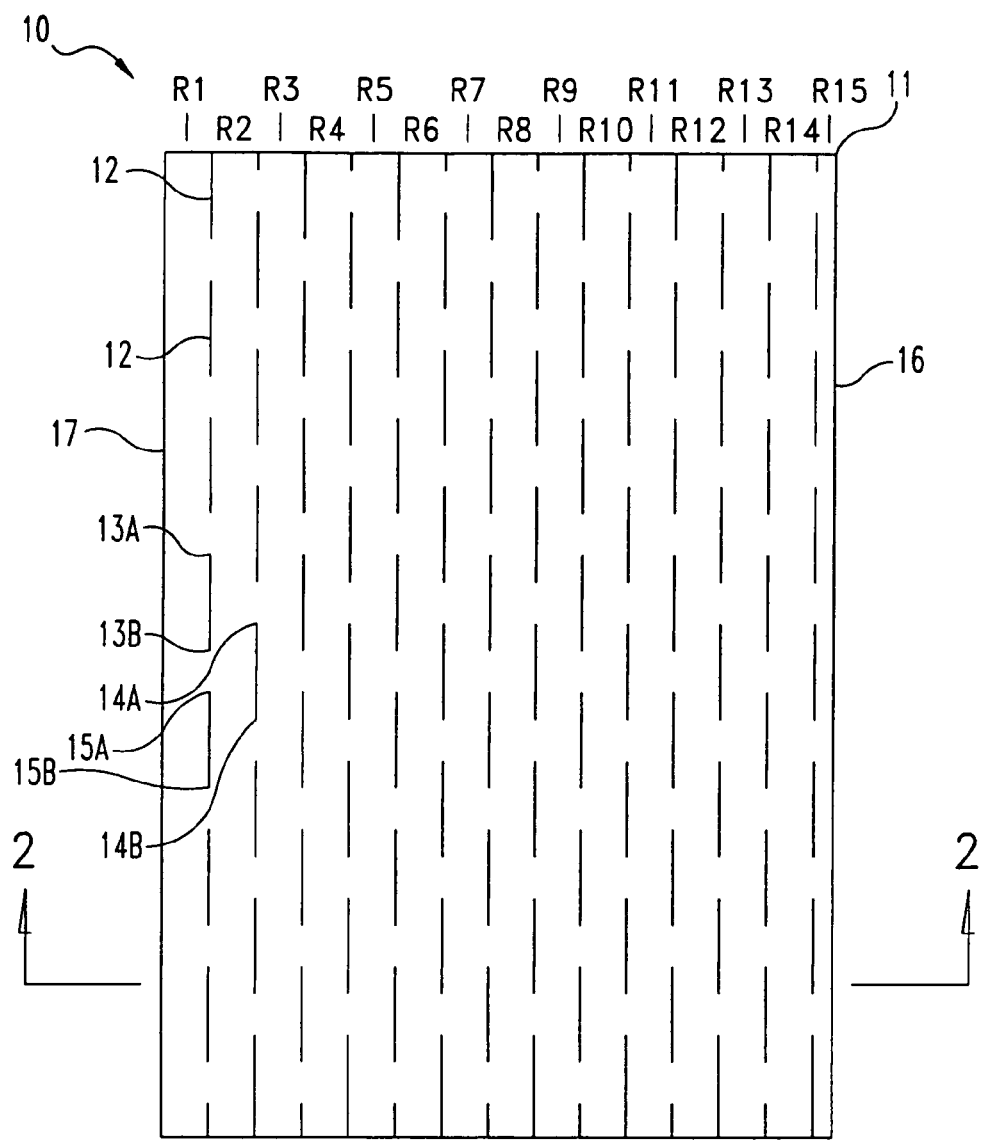
FIG. 1 shows a meshed tissue graft device of the invention containing multiple, bonded submucosa or renal capsule membrane layers.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, the present invention provides a tissue graft product that includes a meshed collagen-containing layer comprised of submucosa or renal capsule tissue. The product, in its preferred form, will have multiple slits therein to provide the mesh pattern, and in turn the mesh pattern will provide deformability to the collagen-containing layer, for example exhibiting an expansion ratio of at least about 1.2:1 when hydrated. The invention also provides grafting methods utilizing such tissue graft products, and particularly advantageous methods involve the treatment of externally exposed wounds such as burn wounds to the skin. The invention also provides methods of manufacturing such submucosa and/or renal capsule constructs, and medical articles that include such constructs enclosed within sterile packaging.

The preferred medical graft products of the invention will include submucosa tissue or renal capsule membrane tissue, such as submucosa tissue or renal capsule membrane tissue derived from a warm-blooded vertebrate. Mammalian submucosa or renal capsule membrane tissues are preferred. In particular, tissues derived from animals raised for meat or other product production, e.g. pigs, cattle or sheep, will be advantageous. Porcine submucosa or renal capsule membrane tissue provides a particularly preferred starting material for use in the present invention.

The submucosa can be derived from any suitable organ or other biological structure, including for example submucosa tissues derived from the alimentary, respiratory, intestinal, urinary or genital tracts of warm blooded vertebrates. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made to U.S. Pat. Nos. 4,902,508, 5,554,389, 5,993,844, 6,206,931, and 6,099, 567. The renal capsule tissue can also be obtained from warm blooded vertebrates, as described more particularly in copending U.S. patent application Ser. No. 10/186,150 filed Jun. 28, 2002 and copending International patent application serial No. PCT/US02/20499 filed Jun. 28, 2002. The submucosa or renal capsule membrane can retain its original native crosslinking, and/or may be crosslinked with suitable crosslinking agents as disclosed for example in U.S. Pat. No. 5,733,337.

As prepared, the submucosa or renal capsule membrane tissue may optionally retain growth factors or other bioactive components native to the source tissue. For example, the submucosa tissue or renal capsule tissue may include one or more growth factors such as basic fibroblast growth factor (FGF-2), transforming growth factor beta (TGF-beta), epidermal growth factor (EGF), and/or platelet derived growth factor (PDGF). As well, submucosa or renal capsule membrane tissue used in the invention may include other biological materials such as heparin, heparin sulfate, hyaluronic acid, fibronectin and the like. Thus, generally speaking, the submucosa or renal capsule membrane tissue may include a bioactive component that induces, directly or indirectly, a cellular response such as a change in cell morphology, proliferation, growth, protein or gene expression. Further, in addition or as an alternative to the inclusion of such native bioactive components, non-native bioactive components such as those synthetically produced by recombinant technology or other methods, may be incorporated into the submucosa or renal capsule membrane tissue.

Submucosa tissue used in the invention is preferably highly purified, for example, as described in U.S. Pat. No. 6,206,931. Thus, preferred material will exhibit an endotoxin level of less than about 12 endotoxin units (EU) per gram, more preferably less than about 5 EU per gram, and most preferably less than about 1 EU per gram. As additional preferences, the submucosa material may have a bioburden of less than about 1 colony forming units (CFU) per gram, more preferably less than about 0.5 CFU per gram. Fungus levels are desirably similarly low, for example less than about 1 CPU per gram, more preferably less than about 0.5 CFU per gram. Nucleic acid levels are preferably less than about 5 µg/mg, more preferably less than about 2 µg/mg, and virus levels are preferably less than about 50 plate forming units (PFU) per gram, more preferably less than about 5 PFU per gram. These and additional properties of submucosa tissue taught in U.S. Pat. No. 6,206,931 may be characteristic of the submucosa tissue used in the present invention. Preferred renal capsule tissue used in the invention will also have the above-mentioned characteristics relative to endotoxin, bioburden, fungus, nucleic acid and virus levels.

A typical layer thickness for the as-isolated submucosa layer used in the invention ranges from about 50 to about 250 microns when fully hydrated, more typically from about 50 to about 200 microns when fully hydrated. A typical layer thickness for the as-isolated renal capsule tissue used in the invention ranges from about 70 to about 100 microns, more typically about 80 microns. These layer thicknesses may vary with the type and age of the animal used as the tissue source. As well, these layer thicknesses may vary with the source of the tissue obtained from the animal source.

Submucosa tissue or renal capsule tissue used in the invention may be free of additional, non-native crosslinking, or may contain additional crosslinking. Such additional crosslinking may be achieved by photo-crosslinking techniques, by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

When additionally crosslinked, submucosa or renal capsule tissues of the invention can be additionally crosslinked internally within a single layer, and/or crosslinking may be used in whole or in part to bond multiple submucosa layers to one another. Thus, additional crosslinking may be added to individual submucosa or renal capsule layers prior to bonding to one another, during bonding to one another, and/or after bonding to one another.

Meshed medical devices of the invention may include for example a single submucosa or renal capsule tissue layer, or may include a plurality (two or more) of submucosa or renal capsule tissue layers bonded to one another, to provide the overall collagen layer. Preferred devices of the invention will include multiple submucosa or renal capsule tissue layers bonded to one another so as to provide an overall collagen layer thickness of at least about 150 microns, typically ranging from about 150 to about 1000 microns, and in certain embodiments ranging from about 200 to about 1000 microns. Such relatively thick layers, when meshed in accordance with the invention, provide particularly advantageous and lasting collagen scaffolds for tissue ingrowth, especially in the field of wound care such as burn and wound care. In addition to such thicknesses, typical tissue graft products of the invention in sheet-form will have lengths and widths ranging from about 2 cm to about 50 cm.

In accordance with the invention, the submucosa-containing or renal capsule-containing collagen layer will preferably be processed so as to exhibit a meshed structure. Such a meshed structure will have a plurality of slits therein to provide a mesh pattern, and the mesh pattern will provide deformability to the structure, especially expandability. In this regard, in the preferred constructs, expansion or other deformation of the meshed structure will widen the openings created by the slits of the mesh pattern, by lateral and/or vertical displacement of the edges of the slits relative to one another. Preferred devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the graft product, particularly in the field of wound care.

Figure 2:
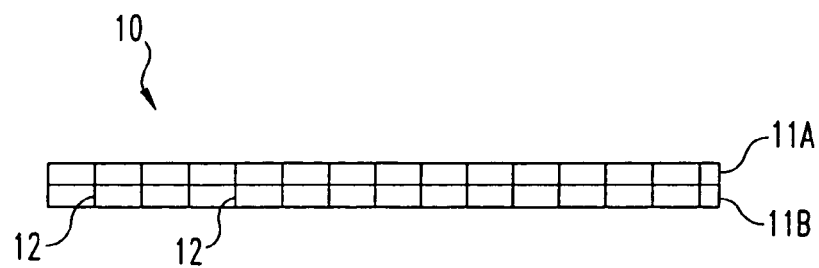
FIG. 2 provides a cross-sectional view of the meshed tissue graft device of FIG. 1 taken along line 2-2 and viewed in the direction of the arrows.

With reference now to FIG. 1, shown is an illustrative meshed tissue graft device of the present invention. The graft device 10 includes a layer of collagen 11 comprised of submucosa tissue or renal capsule tissue. Illustratively, layer 11 can be formed from a single submucosa or renal capsule tissue layer, but is preferably formed from a plurality of submucosa or renal capsule tissue layers. With reference to FIG. 2, shown is a cross sectional view of device 10 taken along line 2-2 and viewed in the direction of the arrows. Shown is layer 11 including a first submucosa or renal capsule layer 11A bonded to a second submucosa or renal capsule layer 11B to form a substantially unitary collagen-containing layer 11. In this regard, it is understood that FIG. 2 is illustrative but not limiting of the invention, and that the collagen layer 11 can also be made of more than two submucosa or renal capsule layers, for example at least three, four, five, six, seven, or eight or more submucosa or renal capsule tissue layers. In this fashion, devices of varying thickness, strengths, and longevity upon implantation can be produced.

With reference again to FIG. 1, collagen layer 11 includes a meshed pattern formed by a plurality of slits 12 created in layer 11. In particular slits 12 are arranged in a plurality of relatively parallel rows R1 through R14. The termini of the slits in a particular row are offset relative to the termini of the slits in an adjacent row. In addition, the termini of slits in an adjacent row occur along the length of the slits in an adjacent row when considered in the lateral direction. Thus, the termini 13A and 13B of a slit in R1 are staggered relative to the termini 14A and 14B of a slit in R2, considered in the longitudinal direction (in which the elongate slits run vertical in FIG. 1). On the other hand, considered in a second lateral direction (90° to the first direction), the termini 14A and 14B of slits in R2 fall within the length of the slits in R1—i.e., between termini 13A and 13B and termini 15A and 15B. Having the slits in this arrangement provides a meshed collagen layer 11 which is substantially deformable or expandable in the horizontal direction of FIG. 1. That is, upon applying an outward force to the material to increase the distance between edges 16 and 17 of the layer 11, the material deforms so as to expand in the horizontal direction. As the material expands, the slits 12 of the layer 11 are widened by lateral and/or vertical movement of the slit edges relative to one another, thus expanding the openings provided by slits 12. In particular, in the mesh pattern shown in FIG. 1, such expansion to a substantial extent will create generally hexagonal shape openings in the meshed device 10. It has been found that these and other meshed structures which provide for deformability of the device 10 significantly improve the properties of the device 10 for use in tissue grafting, and for wound care in particular. Importantly, such deformability and expandability of the openings defined by slits 12 facilitates high level drainage of wounds to which the material is applied. In addition, the meshed structure provides deformability to the external dimensions of device 10 so that upon its application it can be expanded or deformed to improve the size and/or shape of the material for application to the wound.

The meshed structure of the device 10 or other meshed patterns can be created using suitable meshing devices designed for processing skin autograft sections. Such devices typically include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-through put method of preparing meshed submucosa or renal capsule devices of the invention. It will be understood, however, that the mesh pattern can be made by hand-cutting the material or by using appropriate cutting tools with multiple blades to cut the slits to provide the mesh pattern.

Figure 3:
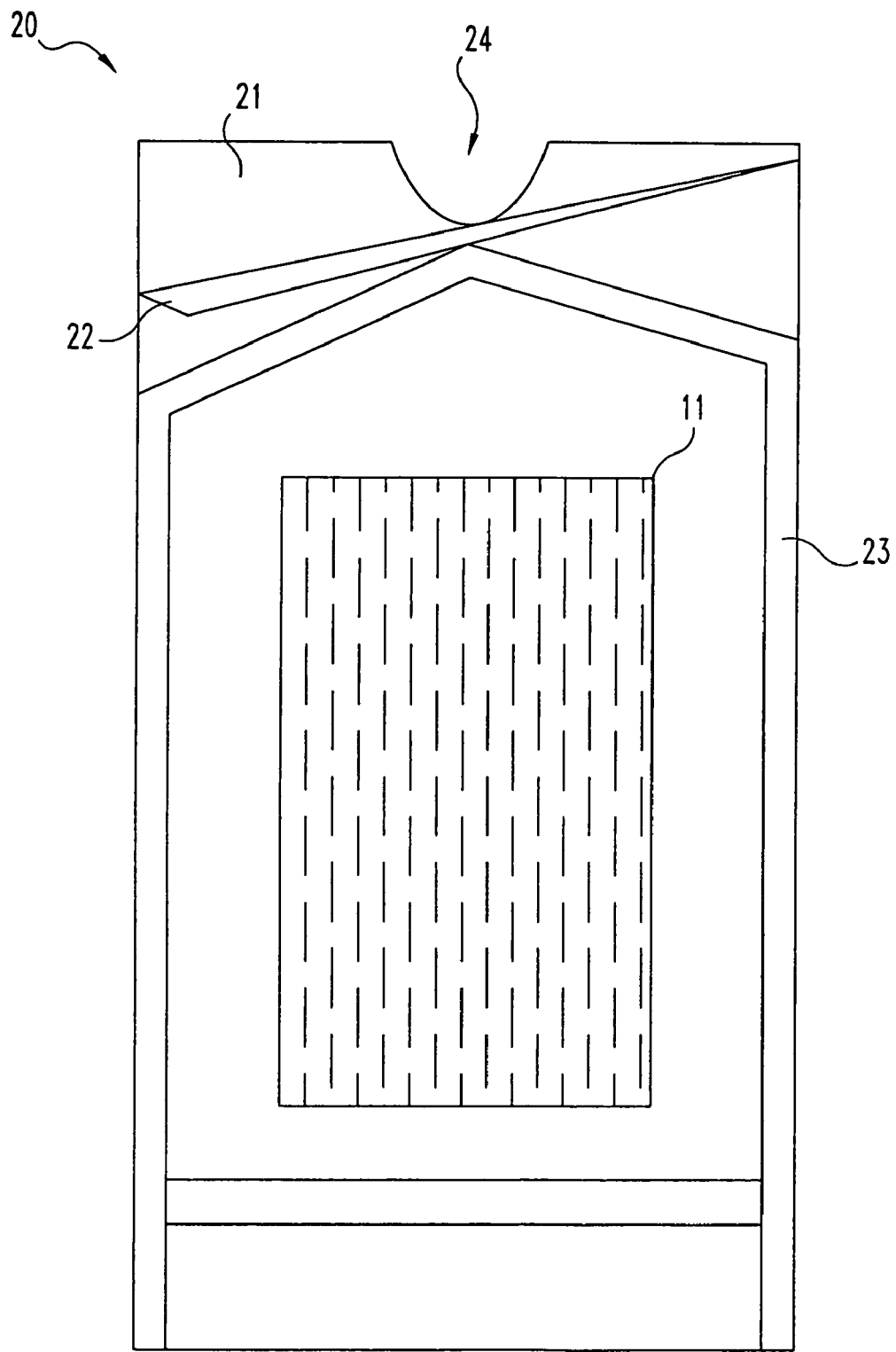
FIG. 3 shows a medical product of the invention including a meshed tissue graft device of FIG. 1 enclosed within a sterile medical package.

With reference now to FIG. 3, shown is a medical product of the invention including meshed graft device 10 sealed within sterile medical packaging. In particular, medical product 20 has packaging including a backing layer 21 and a front film layer 22 (shown partially drawn away from backing layer 21). Graft device 11 is sealed between backing layer 21 and film 22 utilizing a boundary of pressure-adhesive 23 as is conventional in medical packaging. A cut-out 24 may be provided in the backing layer 21 to assist a user in separating the film layer 22 from the backing layer 21.

The final, packaged product is provided in a sterile condition. This may be achieved, for example, by irradiation, ethylene oxide gas, or any other suitable sterilization technique, and the materials and other properties of the medical packaging will be selected accordingly.

Meshed graft devices of the invention can be used in grafting applications for treatment of human or other animal conditions. In one preferred application, the meshed materials of the invention are used in the treatment of wounds and in particular open, cutaneous wounds. Open, cutaneous wounds may be classified into one of four grades depending on the depth of the wound. A Grade I wound is limited to the epithelium. A Grade II wound extends into the dermis. A Grade III wound extends into the subcutaneous tissue; and, a Grade IV wound (or full-thickness wound) exposes bone. The term "partial thickness wound" refers to wounds that encompass Grades I-III; examples of partial thickness wounds include burn wounds, pressure sores, venous stasis ulcers, and diabetic ulcers. An especially advantageous application of meshed products of the invention is in the treatment of partial thickness open cutaneous wounds, including burns and ulcers. These wounds are often chronic (e.g. lasting at least about 30 days untreated), and benefit significantly from the application of meshed graft products of the present invention. Burn and ulcer wounds also exude fluids at a high level. Graft products of the invention will allow passage of the significant exudant, which facilitates maintenance of the graft products in contact with the wounded tissue, rather than floating off the wound tissue.

In use, the physician, veterinarian or other user of the devices of the invention will prepare the wound for treatment in a conventional fashion, which may for example include cleaning and/or debridement of the wound with water, physiologic saline or other solutions, and potentially also treating the wound with antibiotics or other therapeutic agents. The meshed device of the invention will be applied to the wound in a fashion to facilitate and promote healing of the wound. In this regard, the meshed device may be applied in a dehydrated, partially hydrated, or fully hydrated state. Once grafted, the meshed material of the invention will hydrate (if not previously hydrated) and remain generally in place either alone or in combination with other wound dressing materials applied below or on top of the meshed material. In the treatment of open cutaneous wounds, it has been found that meshed, single-submucosa-layer devices are quickly resorbed by the body and do not provide a most beneficial, lasting matrix for tissue ingrowth. Therefore, wound repair devices of the invention will preferably include a plurality of submucosa layers bonded to one another, to provide a lasting matrix. The layer bond may be achieved, for example, by one or more of chemical crosslinking as discussed above, dehydrothermal bonding under conditions of freeze drying or vacuum pressing, bonding agents, or other known techniques. The need for a thicker, lasting matrix has been found to be particularly acute in chronic burns or ulcers wherein continuous, prolonged wound coverage and healing are paramount. A similar layer-bonding and meshing technique can be used with other relatively thin, resorbable extracellular matrix layers, which also form a part of the present inventive embodiment.

For the purpose of promoting a further understanding of the present invention and its features and advantages, the following specific examples are provided. It will be understood that these examples are illustrative, and not limiting, of the invention.

EXAMPLE 1

A thirty-foot long section of whole intestine from a mature adult hog is rinsed with water. This material is then treated in a 0.2 percent by volume peracetic acid in a 5 percent by volume aqueous ethanol solution for a period of two hours with agitation. The tela submucosa layer is then delaminated in a disinfected casing machine from the whole intestine. The delaminated tela submucosa is rinsed four times with sterile water and tested for impurities or contaminants such as endotoxins, microbial organisms, and pyrogens. The resultant tissue was found to have essentially zero bioburden level. The tela submucosa layer separated easily and consistently from the whole intestine and was found to have minimal tissue debris on its surface.

EXAMPLE 2

A unitary collagen layer containing two dehydrothermally or chemically bonded submucosa or renal capsule layers is processed as follows. The layer, in a dried state, is processed with a skin graft mesher available from Padgett Instruments, set at an expansion ratio of 4:1. The resulting double-layer, meshed medical device exhibits satisfactory properties, and an expansion ratio of at least 2:1 when hydrated. When applied to a wound, such as a burn or ulcer wound, the meshed medical construct of this Example provides a highly drained yet lasting scaffold and protective layer to promote healing of the wound.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all patents and other publications cited herein are indicative of the abilities of those ordinarily skilled in the art, and each such patent and publication is hereby incorporated herein by reference in its entirety as if individually incorporated by reference and fully set forth.

What is claimed is:

1. A medical product, comprising:
a sterile package; and
a sterile tissue graft product contained within said sterile package, said tissue graft product exhibiting a non-tubular, sheet form and being useful for treating an exuding open cutaneous wound, the sterile tissue graft product having a thickness extending between a top outermost surface of the sterile tissue graft product and a bottom outermost surface of the sterile tissue graft product, wherein an extracellular matrix material obtained from a biological tissue source spans the entirety of said thickness and has a plurality of slits therein providing a mesh pattern, said mesh pattern effective to provide an expansion ratio of at least about 1.2:1 to said extracellular matrix material in a hydrated condition, the extracellular matrix material including submucosa or renal capsule tissue retaining growth factors native to the biological tissue source and having a nucleic acid level of less than 5 micrograms per milligram.

2. A tissue graft product according to claim 1, wherein said extracellular matrix material comprises intestinal submucosa, stomach submucosa, urinary bladder submucosa, or uterine submucosa.

3. A tissue graft product according to claim 2, wherein said extracellular matrix material comprises small intestinal submucosa.

4. A tissue graft product according to claim 1, wherein said extracellular matrix material comprises at least two submucosa layers, said submucosa layers bonded together.

5. The tissue graft product according to claim 4, wherein said submucosa layers are bonded together by a chemical crosslinker.

6. The tissue graft product according to claim 4, wherein said submucosa layers are bonded together in the absence of a chemical crosslinker.

7. The tissue graft product according to claim 6, wherein said submucosa layers are bonded together by dehydration bonding.

8. The tissue graft product according to claim 4, wherein said submucosa layers are bonded to form a substantially unitary collagen layer.

9. The tissue graft product according to claim 8, wherein said submucosa layers are bonded over substantially the entire area in which they contact one another.

10. A tissue graft product according to claim 4, wherein said submucosa layers retain basic fibroblast growth factor (FGF-2) native to the biological tissue source.

11. A tissue graft product according to claim 4, wherein said mesh pattern is effective to provide an expansion ratio of at least about 2:1 to said extracellular matrix material in a hydrated condition.

12. A tissue graft product according to claim 11, wherein said submucosa layers each have a thickness of about 50 microns to about 200 microns in a hydrated condition.

13. A tissue graft product according to claim 12, wherein said submucosa or renal capsule tissue additionally retains heparin sulfate, hyaluronic acid and fibronectin from the biological tissue source.

14. A tissue graft product according to claim 1, wherein said expansion ratio is at least about 2:1.

15. A tissue graft product according to claim 1, wherein said expansion ratio is at least about 3:1.

16. A tissue graft product according to claim 1, wherein said submucosa or renal capsule tissue additionally retains heparin sulfate, hyaluronic acid and fibronectin from the biological tissue source.

17. The tissue graft product of claim 1, wherein said extracellular matrix material comprises an extracellular matrix layer harvested from the biological tissue source and not subjected to a chemical crosslinker.

18. The tissue graft product of claim 1, wherein said submucosa or renal capsule tissue retains transforming growth factor beta (TGF-beta) native to the biological tissue source.

19. A method for preparing a sterile tissue graft product having a thickness extending between a top outermost surface of the tissue graft product and a bottom outermost surface of the tissue graft product, the method comprising:
provide a sterile package;
providing a sterile tissue graft product contained within said sterile package and exhibiting a non-tubular, sheet form, said tissue graft product comprising an extracellular matrix material that is obtained from a biological tissue source and that includes submucosa or renal capsule tissue retaining growth factors native to the biological tissue source and having a nucleic acid level of less than 5 micrograms per milligram; and
producing in said extracellular matrix material a plurality of slits, said slits providing a mesh pattern, said mesh pattern effective to provide an expansion ratio of at least about 1.2:1 to said extracellular matrix material in a hydrated condition, wherein said extracellular matrix material spans the entirety of said thickness.

20. A method according to claim 19, wherein said extracellular matrix material includes at least two submucosa layers, said submucosa layers bonded to one another.

21. A method according to claim 20, wherein said submucosa layers are dehydrothermally bonded to one another.

22. A method according to claim 20, wherein said submucosa layers are bonded to one another with a chemical crosslinker.

23. A method according to claim 20, wherein said mesh pattern is effective to provide an expansion ratio of at least about 2:1 to said extracellular matrix material in a hydrated condition.

24. The method claim 19, wherein said submucosa or renal capsule tissue additionally retains heparin sulfate, hyaluronic acid and fibronectin from the biological tissue source.

25. A medical product, comprising:
a sterile package; and
a sterile tissue graft construct contained within said sterile package, said tissue graft construct exhibiting a non-tubular, sheet form and having a thickness extending between a top outermost surface of the sterile tissue graft product and a bottom outermost surface of the sterile tissue graft construct, the tissue graft construct comprising:
at least two extracellular matrix material layers obtained from a biological tissue source and bonded to one another to provide a multi-layer construct, the at least two extracellular matrix material layers having a nucleic acid level of less than 5 micrograms per milligram and retaining growth factors native to the biological tissue source;
said at least two extracellular matrix material layers spanning the entirety of said thickness and having a plurality of slits therein providing a mesh pattern, said mesh pattern effective to provide an expansion ratio of at least about 1.2:1 to said extracellular matrix material in a hydrated condition, the extracellular matrix material including submucosa or renal capsule tissue.

26. A tissue graft construct according to claim 25, wherein said at least two extracellular matrix material layers comprise at least two submucosa layers, said submucosa layers bonded to one another.

27. A tissue graft product according to claim 26, wherein said submucosa is intestinal submucosa, stomach submucosa, urinary bladder submucosa, or uterine submucosa.

28. A tissue graft product according to claim 27, wherein said submucosa is small intestinal submucosa.

29. A tissue graft product according to claim 25, wherein said mesh pattern is effective to provide an expansion ratio of at least about 2:1 to said at least two extracellular matrix material layers in a hydrated condition.

30. The tissue graft construct of claim 25, wherein said extracellular matrix layers are bonded together in the absence of a chemical crosslinker.

31. The tissue graft construct of claim 30, wherein said extracellular matrix layers are bonded together by dehydration.

32. A medical product, comprising:
a sterile package; and
a dried, sterile tissue graft product contained within said sterile package, said dried, sterile tissue graft product exhibiting a non-tubular, sheet form and having a thickness extending between a top outermost surface of the dried, sterile tissue graft product and a bottom outermost surface of the dried, sterile tissue graft product, wherein an extracellular matrix material obtained from a biological tissue source spans the entirety of said thickness and has a plurality of slits therein providing a mesh pattern, said mesh pattern effective to provide an expansion ratio of at least about 1.2:1 to said extracellular matrix material when the extracellular matrix material is in a hydrated condition, the extracellular matrix material including submucosa or renal capsule tissue retaining growth factors native to the biological tissue source and having a nucleic acid level of less than 5 micrograms per milligram.

33. The medical product of claim 32, wherein said submucosa or renal capsule tissue additionally retains heparin sulfate, hyaluronic acid and fibronectin from the biological tissue source.

34. A medical product, comprising:
a sterile package; and
a sterile tissue graft product contained within said sterile package, said tissue graft product exhibiting a non-tubular, sheet form and being useful for treatment of an exuding, open cutaneous wound, the sterile tissue graft product having a thickness extending between a top outermost surface of the sterile tissue graft product and a bottom outermost surface of the sterile tissue graft product, wherein an extracellular matrix material obtained from a biological tissue source spans the entirety of said thickness and has a plurality of slits therein providing a mesh pattern, the extracellular matrix material including submucosa or renal capsule tissue retaining growth factors native to the biological tissue source and having a nucleic acid level of less than 5 micrograms per milligram, said slits sufficient in number and spacing to allow drainage when applied to the exuding open cutaneous wound so as to maintain contact between tissue of the wound and the tissue graft product, wherein said mesh pattern is effective to provide an expansion ratio of at least about 1.2:1 to said extracellular matrix material in a hydrated condition.

35. The tissue graft product of claim 34, wherein said submucosa or renal capsule tissue additionally retains heparin sulfate, hyaluronic acid and fibronectin from the biological tissue source.

* * * * *